United States Patent
Bagchi et al.

(10) Patent No.: US 7,335,651 B2
(45) Date of Patent: Feb. 26, 2008

(54) COMPOSITIONS INCORPORATING(-)-HYDROXYCITRIC ACID AND RELATED METHODS FOR PROMOTING FAT OXIDATION

(75) Inventors: Debasis Bagchi, Concord, CA (US); Harry G. Preuss, Fairfax Station, VA (US); Sunny E. Ohia, Pearland, TX (US)

(73) Assignee: Interhealth Nutraceuticals Incorporated, Benicia, CA (US)

( * ) Notice: Subject to any disclaimer, the term of this patent is extended or adjusted under 35 U.S.C. 154(b) by 0 days.

(21) Appl. No.: 10/911,095

(22) Filed: Aug. 3, 2004

(65) Prior Publication Data

US 2005/0008722 A1 Jan. 13, 2005

Related U.S. Application Data

(62) Division of application No. 10/325,675, filed on Dec. 20, 2002.

(60) Provisional application No. 60/343,473, filed on Dec. 20, 2001.

(51) Int. Cl.
*A61K 31/555* (2006.01)
*A61K 31/19* (2006.01)
*A61K 36/00* (2006.01)

(52) U.S. Cl. .................. 514/188; 514/574; 424/777

(58) Field of Classification Search ............... 424/777; 514/188, 574
See application file for complete search history.

(56) References Cited

U.S. PATENT DOCUMENTS

| | | | |
|---|---|---|---|
| 3,764,692 A | 10/1973 | Lowenstein | |
| 4,923,855 A | 5/1990 | Jensen | |
| 4,954,492 A | 9/1990 | Jensen | |
| 5,116,820 A | 5/1992 | Hiji | |
| 5,194,615 A | 3/1993 | Jensen | |
| 5,266,560 A | 11/1993 | Furman et al. | |
| 5,480,657 A | 1/1996 | Allen | |
| 5,536,516 A | 7/1996 | Moffett et al. | |
| 5,543,405 A | 8/1996 | Keown et al. | |
| 5,567,424 A | 10/1996 | Hastings | |
| 5,612,039 A | 3/1997 | Policappelli et al. | |
| 5,626,849 A | 5/1997 | Hastings et al. | |
| 5,656,314 A | 8/1997 | Moffett et al. | |
| 5,716,976 A | 2/1998 | Bernstein | |
| 5,783,603 A * | 7/1998 | Majeed et al. ............... | 514/574 |
| 5,905,075 A | 5/1999 | Harpe et al. | |
| 5,911,992 A | 6/1999 | Braswell et al. | |
| 5,981,510 A | 11/1999 | Fujiwara et al. | |
| 6,034,125 A | 3/2000 | McLeod | |
| 6,048,846 A | 4/2000 | Cochran | |
| 6,100,251 A | 8/2000 | De la Harpe et al. | |
| 6,160,172 A | 12/2000 | Balasubramanyam et al. | |
| 6,203,819 B1 | 3/2001 | Fine | |
| 6,207,714 B1 * | 3/2001 | Clouatre et al. ............ | 514/574 |
| 6,217,898 B1 | 4/2001 | Cavazza | |
| 6,258,848 B1 | 7/2001 | Fantus | |
| 6,291,533 B1 | 9/2001 | Fleishner | |
| 6,352,713 B1 | 3/2002 | Kirschner et al. | |
| 6,383,482 B1 | 5/2002 | Gorsek | |
| 6,395,296 B1 | 5/2002 | Balasubramanyam et al. | |
| 6,399,089 B1 | 6/2002 | Yegorova et al. | |
| 6,413,545 B1 | 7/2002 | Alviar et al. | |
| 6,420,350 B1 | 7/2002 | Fleischner | |
| 6,441,041 B1 | 8/2002 | Clouatre et al. | |
| 6,447,807 B1 | 9/2002 | Clouatre et al. | |
| 6,476,071 B1 | 11/2002 | Clouatre et al. | |
| 6,482,858 B1 | 11/2002 | Clouatre et al. | |
| 6,541,026 B2 | 4/2003 | Siskind | |
| 6,579,866 B2 | 6/2003 | McCleary | |
| 6,589,566 B2 | 7/2003 | Ueda et al. | |
| 6,638,542 B2 | 10/2003 | Nieuwenhuizen et al. | |
| 6,809,115 B2 | 10/2004 | Katz et al. | |
| 6,967,030 B2 | 11/2005 | Wright et al. | |
| 2001/0031744 A1 | 10/2001 | Kosbab | |
| 2001/0044469 A1 | 11/2001 | Clouatre et al. | |
| 2002/0132219 A1 | 9/2002 | McCleary | |
| 2003/0119913 A1 | 6/2003 | Ohia et al. | |
| 2003/0133992 A1 | 7/2003 | Bagchi et al. | |
| 2003/0207942 A1 | 11/2003 | Bhaskaran et al. | |

(Continued)

FOREIGN PATENT DOCUMENTS

EP 0 714 663 6/1996

(Continued)

OTHER PUBLICATIONS

Stedman's Medical Dictionary, 25th edition, published 1990 by Williams & Wilkins (MD), p. 1076, "Obesity".*

(Continued)

*Primary Examiner*—Raymond J. Henley, III
(74) *Attorney, Agent, or Firm*—Marshall, Gerstein & Borun LLP

(57) ABSTRACT

Methods for promoting healthy body weight and improving a variety of related physiological factors, including serum serotonin levels, serum leptin levels, fat oxidation, cholesterol levels, and body mass index, in persons or other mammals, include administering to those persons or other mammals effective amounts of hydroxycitric acid or a combination of hydroxycitric acid, chromium and gymnemic acid, which work synergistically to further to promote healthy body weight and improve these physiological factors.

15 Claims, No Drawings

U.S. PATENT DOCUMENTS

| | | | |
|---|---|---|---|
| 2003/0220329 | A1 | 11/2003 | Surwit et al. |
| 2004/0014692 | A1 | 1/2004 | Bagchi et al. |
| 2004/0157929 | A1* | 8/2004 | Ohia et al. .................. 514/574 |
| 2004/0186181 | A1 | 9/2004 | Bagchi et al. |

FOREIGN PATENT DOCUMENTS

| | | |
|---|---|---|
| JP | 10262610 | 10/1998 |
| WO | WO 89/10357 | 11/1989 |
| WO | WO 98/28989 | 7/1998 |
| WO | WO 99/03464 | 1/1999 |
| WO | WO 00/12080 | 3/2000 |
| WO | WO 00/48983 | 8/2000 |
| WO | WO 00/57729 | 10/2000 |
| WO | WO 02/078616 A2 | 10/2002 |

OTHER PUBLICATIONS

Apr. 1969, Physiological Reviews, Chromium Occurrence and Function in Biological Systems, by Mertz, pp. 163-239.

Jan. 1977, Influence of (-) -hydroxycitrate on lipigenesis in chickens and rats, by Romsos, 1 page.

1981, Role of fatty acid synthesis in the control of insulin-stimulated glucose utilization by rat adipocytes, by Susan Fried, et al., pp. 753-762.

1991, Implication of Steroid Saponins and Sapogenins in the Hypocholesterolemic Effect of Fenugreek, by Yves Sauvaire et al., 7 pages.

Jun. 1992, Antidiabetic effects of S-allyl cysteine sulphoxide isolated from garlic Allium sativum Linn, by Sheda et al., pp. 523-526.

1994, More direct evidence for a malonyl-CoA-carnitine palmitoyltransferase I interaction as a key event in pancreatic beta-cell signaling, by Chen et al., pp. 878-883.

Jun. 1994, Effects of chromium and guar on sugar-induced hypertension in rats, by Preuss et al., pp. 170-177.

Jul. 1994, More direct evidence for a malonyl-CoA-carnitine palmitoyltransferase I interation as a key event in pancreative beta-cell signaling, by Chen et al., 1 page.

Sep. 1995, Clouatre Consulting Group, New Information on (-)-Hydroxycitric Acid/HCA, by Clouatre, 2 pages.

1998, Current Zinc Intake and Risk of Diabetes and Coronary Artery Disease and Factors Associated with Insulin resistance in Rural and Urban Populations of North India, by Singh et al., pp. 564-570.

Apr. 1999, Toward a wholly nutritional therapy for type 2 diabetes, by McCarty, 2 pages.

Oct. 1999, Leptin increases serotonin turnover by inhibition of brain nitric oxide synthesis, by Calapai et al., pp. 975-982.

2000, Separate systems for serotonin and leptin in appetite control, by Halford et al., pp. 222-232.

Apr. 2000, Separate systems for serotonin and leptin in appetite control, by Halford et al., 1 page.

Mar. 2001, Increase of fat oxidation and weight loss in obese mice caused by chronic treatment with human growth hormone or a modified C-terminal fragment, by Heffernan et al., pp. 1442-1449.

Jan. 2004, Clinical Study on Ephedra-Free Super Citrimax Published in Nutrition Research, 4 pages.

Researchers Reveal the Beauty of Super Citrimax—Again, 8 pages, (Feb. 23, 2004).

(-)-Hydroxycitrates The usefulness of (-)-hydroxycitric acid as an obesity regulator is attracting more attention from the food & pharmaceutical industry. Can it be called an ingredient for functional foods? by Verghese, pp. 38-40, no date available.

The Diet and Health Benefits of HCA (Hydroxycitric Acid) How This All-Natural Diet Aid Promotes Weight Loss and Inhibits Fat Production, by Clouatre et al., pp. 23-27, no date available.

U.S. Appl. No. 60/554,653, filed Mar. 19, 2004, Bagchi et al.

U.S. Appl. No. 60/628,381, filed Nov. 16, 2004, Bagchi et al.

U.S. Appl. No. 09/463,024, filed Feb. 14, 2002, G. Ganga Raju.

Clouatre, Dallas, "Anti-Fat Nutrients," Pax Publishing, San Francisco, CA (1993).

Clouatre, Dallas, "New Information on (-)-hydroxycitric acid/HCA," Clouatre Consulting Group (Sep. 5, 1995).

Goldberg, Burton, "Weight Loss—An alternative Medicine Definitive Guide," AlternativeMedicine.com Books, Tiburon, California, (2000).

Kendall, Pat, "Beware of New Weight Loss Products," Food Science and Human Nutrition Specialist, Colorado State University Cooperative Extension (Jul. 7, 1999).

Murray, Michael T., Encyclopedia of Nutritional Supplements, The Essential Guide for Improving your Health Naturally,: Prima Publishing, Random House, Inc., New York. pp. 194-198 (1996).

Ohia, Sunny E., et al., "Safety and mechanism of appetite suppression by a novel hydroxycitric acid extract (HCA-SX)," *Molecular and Cellular Biochemistry*, vol. 238, pp. 89-103, 2002.

Ohia, Sunny E., et al., "Effect of Hydroxycitric Acid on Serotonin Release from Isolated Rat Brain Cortex," Research Communications in Molecular Pathology and Pharmacology, vol. 109, Nos. 3 & 4, March, Apr. 2001, pp. 210-216.

Palmeri, Denise, "Metabolife, Metabolite and Chitoslim: Safe Bets for Losing Weight?," ext.colostate.edu, May 2002 pp. 1-4.

Roy, Sashwati, et al., "Body Weight and Abdominal Fat Gene Expression Profile in Response to a Novel Dydroxycitric Acid-Based Dietary Supplement," *Gene Expression*, vol. 11, pp. 251-262, Feb. 24, 2004.

Shara, Michael, et al., "Physico-chemical properties of a novel (--)-hydroxycitric acid extract and its effect on body weight, selected organ weights, hepatic lipid peroxidation and DNA fragmentation, hematology and clinical chemistry, and histopathological changes over a period of 90 days," *Molecular and Cellular Biochemistry*, vol. 260, pp. 171-186, Oct. 3, 2003.

Wong, Cathy, "Evaluating Natural Weight Loss Supplements, What to Try and What to Avoid," http://altmedicine.about.com/library/weekly; pp. 1-8, printed May 16, 2002.

Yang, et al., "The synthesis aninal experiments and preliminary clinical trial of chrimium (III)-nicotinicacid-amino acids mixed ligand complexes," Database CAPLUS, Sch. Pharm, West China Univ. Med. Sci., (Chengdu, China), AN 1988:542370, (1986).

Herbs and Weight Loss FAQ's; http://herbsforhealth.about.com/library, pp. 1-3 (downloaded May 16, 2002).

McCarty, M.F., "Enhancing central and peripheral insulin activity as a strategy for the treatment of endogenous depression—an adjuvant role for chromium picolinate?," *Medical Hypotheses*, 43: 247-252 (1994).

Tolbert, L.M. et al., "Serotonin induces mapk activation in primary cultures of cortical neurons," *Division of Molecular Psychiatry*, Yale University, New Haven, CT, USA.

AIM Metabolite (1999) AIM International, Inc.

Chee, "Influence of (-)-Hydroxycitrate on Lipogenesis in Chickens and Rats," *The Journal of Nutrition*, 107:112-119 (1977).

Fonkeng, "Electron Paramagnetic Resonance, Kinetics of Formation and Decomposition Studies of (bis(hydroxyethyl)amino-tris(hydroxymethyl)-methane)oxochromate (V): A Model (V) Complex for DNA Damage Studies," *J. Inorg. Biochem.*, 72:163-171 (1998).

Liu, "Synthesis of Cr(IV)-GSH, Its Identification and Its Free Hydroxy Radical Generation: A Model Compound for Cr(VI) Carcinogenecity," *Biochemical & Biophysical Research Communication*, 235:54-58 (1997).

Ortiz, "Effects of the Antidepressant Drug Tianeptine on Plasma and Platelet Serotonin of Depressive and Healthy Controls," *Journal of Affective Disorders*, 29:227-234 (1993).

Roux, "Serotonin Deficiency in Phenylketonuria.Embryopathy," *Toxicology* in Vitro, 9:653-662 (1995).

* cited by examiner

COMPOSITIONS INCORPORATING(-)-HYDROXYCITRIC ACID AND RELATED METHODS FOR PROMOTING FAT OXIDATION

CROSS REFERENCE TO RELATED APPLICATIONS

This is a division of U.S. patent application Ser. No. 10/325,675, filed Dec. 20, 2002, which claims priority from U.S. Provisional Patent Application Ser. No. 60/343,473, filed Dec. 20, 2001.

The present invention relates generally to compositions and related methods for promoting healthy body weight, including reducing excess body weight or maintaining healthy body weight, and improving related health factors, such as cholesterol levels and body mass index, in persons and other mammals.

Excess body weight is becoming more prevalent worldwide at an alarming rate, both in developing and developed countries. Approximately 61 percent of adults in the U.S. are overweight (i.e., having a body mass index (BMI) of greater than 25 $kg/m^2$), while more than 26 percent of U.S. adults are obese (i.e., having a BMI of greater than 30 $kg/m^2$). Obesity is the second leading cause of premature death in the U.S. Approximately 300,000 Americans die each year from complications caused by obesity. According to the World Health Organization, there are over 300 million obese adults worldwide. Environmental and behavioral changes brought about by economic development, modernization and urbanization have been linked to the global rise in obesity in adults and children, the true health consequences of which may not be fully known for years to come. Consumption of western-style diets, low levels of physical activity and sedentary lifestyles generally have been implicated in the worldwide trend of weight gain.

Increase in body weight results from an imbalance between energy intake and expenditure in a person, manifested by excessive expansion of adipose tissue mass in the person. Obesity leads to a number of poor health factors. In particular, obesity increases the risk of high blood pressure, hypertension, type II diabetes, arthritis, elevated cholesterol, and cancer. Although 30-40% of obese people claim they are trying to lose or maintain body weight, their success rate is low. Dietary approaches for the management of excess body weight have been unsuccessful due to improper caloric restriction and/or lack of physical exercise. Low calorie diets can provide for temporary weight loss, but they have not proven themselves as long-term solutions for people trying to lose or maintain weight. Drugs that suppress appetite, reduce food intake, increase energy expenditure and/or affect nutrient partitioning or metabolism have potential efficacy in reducing body weight. Unfortunately, these also frequently are accompanied by adverse side effects, some of which are life threatening.

High blood cholesterol, high blood triglyceride levels, and obesity all are indicators of increased risk for heart disease and other health maladies. In particular, high levels of total cholesterol, LDL cholesterol or triglycerides, as well as low levels of HDL cholesterol, all are risk factors for various cardiovascular diseases. These conditions are exacerbated by many factors, including poor diet, lack of exercise and obesity. Prevalence for obesity can be reflected in excessive eating and also by genetic factors. One method for reducing appetite, and therefore excessive eating, is by raising serotonin levels in a person. Increased brain levels of serotonin, an important neurotransmitter involved in proper brain function, including regulation of sleep and mood, have also been linked with appetite suppression. Also, a known biomarker for genetic propensity of a person toward obesity is serum leptin, a hormone encoded by the gene that regulates body weight. Leptin binds to receptors in the brain, where it activates signals that inhibit food intake and increase energy expenditure. Studies have shown that plasma leptin levels are higher in overweight than in non-overweight individuals, and higher in women than in men.

The methods described above to treat obesity in humans may be applicable to treating other mammals as well, including animals commonly kept as pets, such as dogs and cats. Excess body weight has reached epidemic proportions in, and is the most common nutritional disorder among, pets. It is estimated that 50% of pets (or roughly 60 million animals) in the United States are overweight or obese (a weight ten percent over ideal body weight is considered overweight, and a weight twenty percent over ideal body weight is clinically defined as obese). An extra five pounds on a dog that should weigh 17 pounds or an extra three pounds on a cat that should weight 10 pounds is comparable to an extra 50 pounds on a person who should weigh 170 pounds. Overweight pets are at higher risk of developing health problems such as heart disease, skeletal problems, breathing problems, diabetes and arthritis. Traditionally, weight management in veterinary medicine relies on one or more recommendations. A veterinarian may prescribe high fiber/reduced calorie diets, or advocate other dietary changes focusing on a decrease in overall caloric intake. Another method to manage pet weight is to increase exercise. Untreated obesity can be a devastating condition for a pet, and instituting an obesity-management program will add quality years to a pet's life.

Various methods exist for treating obesity and the other related health factors discussed above, such as improved diet, increased exercise, and various medications. These, however, have not been entirely effective treatments. Diet modification and increased exercise can be difficult for some individuals to maintain for an extended period, and medications introduce the possibility of negative side effects.

One dietary supplement known for promoting weight loss is (−)-hydroxycitric acid (HCA). HCA is an organic acid similar to citric acid that is found in citrus fruits, such as oranges and lemons, but that has remarkably different properties from citric acid. HCA has been shown to reduce appetite, inhibit fat synthesis, and decrease body weight in persons consuming it, without stimulating the central nervous system of those persons. Therefore, ingestion of HCA will not cause nervousness, rapid heart rate, high blood pressure, or insomnia associated with dietary stimulants such as ephedra (Ma-Huang), caffeine or phenylpropanolamine. Furthermore, in acute toxicity tests, HCA has been show to be even safer than citric acid. HCA predominantly is present in the fruit rind of plants in the genus *Garcinia*, such as *Garcinia cambogia* (of the family Guttiferae), a tree native to South and Southeast Asia. The dried fruit rind, also known as Malabar Tamarind, is extensively used in Southern India for culinary purposes. The fruit exhibits a distinctive sour taste and has been used for centuries to make meals more "filling."

HCA has been sold as a dietary supplement since 1994, but research on HCA and its effects stretches back over 30 years. In 1969, researchers demonstrated that HCA is a competitive inhibitor of A TP-citrate lyase, the enzyme responsible for catalyzing the extramitochondrial cleavage of citrate to oxaloacetate and acetyl-CoA, a building block of fatty acid synthesis. A TP-citrate lyase is important in maintaining the acetyl-CoA pool for fatty acid and cholesterol biosynthesis, particularly during the hyperlipogenic nutritional state produced by high carbohydrate feeding. HCA has been shown to be a highly effective inhibitor of fatty acid synthesis by rat liver in vivo. HCA is theorized to reduce food consumption in humans by diverting carbohydrates away from fat synthesis and towards the synthesis of stored energy in the form of glycogen. Increased glycogen levels in the liver and muscles are believed to send a satiety signal to the brain that the body is "full," resulting in reduced appetite and food intake.

Another possible mechanism of action may be HCA's ability to stimulate serotonin release and inhibit its reuptake in the body. Serotonin (5-HT), a vital neurotransmitter, is involved in a wide range of behavioral functions in the body, including mood, sleep and appetite control. Studies have shown that serotonin affects eating behavior and body weight. Increased plasma levels of serotonin are associated with decreased food intake, reduced weight gain and increased energy expenditure. Another benefit of increasing serotonin levels in the body may be in addressing many of the emotional issues overweight people face, including binge eating and depression. It is well established that serotonin and peptides such as neuropeptide Y are involved in the regulation of eating behavior. It is not certain that HCA's ability to curb appetite and reduce food intake derives from these mechanisms. However, as stated above, HCA produces its effects without stimulating the central nervous system, avoiding the related disadvantages of this.

Another possible mechanism of action may be HCA's ability to down-regulate the obesity regulatory gene as determined by serum leptin levels. Leptin is a 167 amino acid protein hormone encoded by the gene that regulates body weight. Synthesized and secreted by adipocytes (fat cells), leptin binds to receptors in the brain, where it activates signals that inhibit food intake and increase energy expenditure. When receptor-binding activity is diminished, a condition called "leptin resistance," plasma leptin levels increase and the leptin loses its ability to inhibit food intake and increase energy expenditure. As stated previously, studies show that plasma leptin levels are higher in overweight than in non-overweight individuals, and higher in women than in men. Leptin is synthesized and secreted by adipocytes, is present in the bloodstream in amounts related to the amount of fat in the body, and acts primarily on the brain to regulate food intake. Leptin has been shown to be able to modulate insulin secretion and action through these receptors. These findings confirm earlier observations of higher leptin levels in obese individuals than in lean individuals.

Another possible mechanism of action may be HCA's ability to increase fat oxidation. Fat metabolites are products of fat degradation. Following exercise or other fat "burning" processes, fat tissue breaks down into small molecular components, including malondialdehyde, formaldehyde, acetaldehyde and acetone. Increased urinary levels of fat metabolites indicates increased fat degradation or "burning." While the majority of studies on HCA have focused on its mechanism of action at the metabolic level, until recently, no studies have investigated its effect on neurotransmitters associated with the control of appetite, hormones associated with the regulation of body weight, nor fat oxidation. Recent studies on the effect of HCA on serum serotonin levels, serum leptin levels, and fat oxidation, are discussed below.

The potential of HCA as an inhibitor of lipogenesis has been examined, and it was demonstrated that HCA curbs appetite, reduces food intake and inhibits fat synthesis. Oral administration of HCA has been shown to significantly depress in vivo lipogenic rates in a dose-dependent manner in the liver, adipose tissue and small intestine. This hepatic inhibition has been shown to be significant for the 8-hour period when control animals demonstrated elevated rates of lipid synthesis. The kinetics of in vivo hepatic lipogenesis reduction were identical after acute or chronic administration of HCA. However, in relevant studies rates of lipogenesis were depressed after chronic administration of HCA for 30 days, thus HCA may help prevent "fat rebound," a common occurrence where most diets fail, resulting in fat regain once the diet is discontinued. Rats receiving HCA consumed less food than the untreated controls, but this decreased caloric intake was not responsible for the drug-induced depression of hepatic lipogenesis, as shown by studies using pair fed rats. In these studies, an acute oral dose of HCA (2.63 mmoles/kg equivalent to roughly 594 mg/kg body weight) given prior to a standardized synthetic meal caused a significant decrease in liver lipogenesis (roughly 70%) for up to 8 hours after the meal. The production of lipids declined not only in the liver, but in the other tissues in which fats are formed from carbohydrates (i.e., small intestine and adipose tissues).

In one experiment, rats were given various amounts of HCA over a thirty day period (in amounts of 2.63, 1.32, 0.66 or 0.17 mmoles/kg/day) once daily, or 0.33 moles/kg twice daily, to demonstrate the effect on body weight gain in growing rats. A dose-related reduction in weight gain was observed in the rats treated with HCA. The decreases were significant at concentrations of 2.63 mmoles/kg once daily or 0.33 mmoles/kg twice daily. Thus, one-fourth the amount of HCA was required to reduce weight gain when administered in two divided doses as compared to a single dose. However, no significant reductions were observed with the single daily administration of 0.17, 0.66 and 1.32 nmoles/kg. This suggests that HCA is rapidly metabolized in the body and that divided doses are more effective than a single dose at inhibiting lipogenesis. Recent studies also have shown that HCA-induced increases in energy expenditure may account, at least in part, for the observed inhibitory effect of HCA on body weight gain in rats.

A particularly preferred HCA composition, marketed under the name Super CitriMax® (and also designated HCA-SX) by InterHealth Nutraceuticals of Benicia, Calif., incorporates a unique form of HCA bound to the minerals calcium and potassium. HCA-SX is described and claimed in published Patent Cooperation Treaty Application WO 99/03464, herein incorporated by reference. This HCA-SX composition contains approximately 60% by weight of HCA, 11% by weight of calcium and 16% by weight of potassium, with the remaining 13% consisting of water and other naturally occurring constituents of the natural *Garcinia* fruit rind. This is in contrast to other, more common forms of HCA, which are not bound to potassium, but instead are bound only to calcium. As a result of being bound also to potassium, HCA-SX is virtually completely water-soluble, and it is more bioavailable than regular HCA compositions incorporating only calcium. HCA-SX is also significantly less hygroscopic than HCA compositions bound only to potassium, contains 60% HCA—twenty percent more HCA than that typically found in HCA compositions geared toward weight loss—and contains less than one percent sodium, which is of particular benefit to people who have high blood pressure or are on a sodium-restricted diet. HCA-SX also is virtually tasteless, odorless and, in solution, colorless, and does not have the aftertaste associated with other HCA compositions, making it ideal for use in functional foods and beverages.

As stated above, HCA-SX is highly bioavailable and easily retained by obese subjects. Using a new rapid and accurate gas chromatography/mass spectrometric method for measuring blood levels of HCA, scientists recently found that blood levels of HCA-SX increased for at least 2 hours and remained in the blood for more than 4 hours after ingestion. Absorption rates varied among subjects. In a separate experiment, the same investigators found that absorption of HCA-SX peaked two hours after administration, and that the compound remained in the blood for more than nine hours after ingestion. Eating a full meal shortly after taking HCA-SX reduced its absorption by about 60%. HCA-SX was detectable in urine, and therefore its concentration could be used to determine relative HCA absorption.

As discussed above, serotonin affects eating behavior and body weight. Increased plasma levels of serotonin are associated with decreased food intake, reduced weight gain and increased energy expenditure. Researchers have shown that HCA-SX increases the release and availability of serotonin from rat brain cortical slices ex vivo, with optimal concentrations at 300 micromolar, as compared to concentrations of 10, 30, 100 and 1,000 micromolar, indicating an optimal effective dose of HCA-SX. Subsequently, human clinical studies have, for the first time, shown that effective doses of HCA-SX significantly increase serum serotonin levels. Because serotonin has been implicated in the regulation of eating behavior and body weight regulation, appetite suppression induced by administration of HCA could be mediated by this serotonin.

As discussed above, leptin is a biomarker for the gene that regulates body weight. Leptin is present in the bloodstream in amounts related to the amount of fat in the body, and acts primarily on the brain to regulate food intake and energy expenditure. Leptin levels are higher in overweight than in non-overweight individuals. Recently, human clinical studies have, for the first time, shown that effective doses of HCA-SX significantly reduce serum leptin levels and, thus, may down-regulate the genetic propensity of a person toward obesity.

As discussed above, a possible mechanism of action may be HCA's ability to increase fat oxidation. Enhanced oxidation of fat, including adipose tissue and triglycerides, is the primary source of the fat metabolites malondialdehyde, formaldehyde, acetaldehyde and acetone. Recently, human clinical studies have shown that effective doses of HCA-SX significantly increase fat oxidation as determined by increases in urinary metabolites malondialdehyde, formaldehyde, acetaldehyde and acetone, and thus may increase fat degradation or "burning."

Another dietary supplement known for use in regulating appetite and modifying body composition is chromium. Chromium is an essential trace element required for normal protein, fat and carbohydrate metabolism. Chromium levels are known to decrease with age, and marginal chromium deficiencies appear to be widespread. Chromium is important for energy production and plays a role in regulating appetite, reducing sugar cravings and increasing lean body mass. Chromium helps insulin metabolize fat, turn protein into muscle and convert sugar into energy. Chromium has been shown to reduce levels of harmful LDL cholesterol, a form of cholesterol linked to heart disease, and increase levels of beneficial HDL cholesterol. Dietary trends that show increased consumption of more highly processed foods may lead to deficiencies of chromium in persons.

Chromium potentiates the action of insulin in vitro and in vivo. Maximal in vitro activity of chromium requires a special chemical form termed Glucose Tolerance Factor (GTF). GTF is a chromium-nicotinic acid (i.e., niacin) complex and is described in, for example, U.S. Pat. Nos. 4,923,855, 4,954,492 and 5,194,615, all to Jensen and herein incorporated by reference. Chromium extracted from Brewers yeast, which is in the GTF form, is absorbed better than inorganic chromium. GTF is transported across the placental barrier, has different tissue distribution from that of inorganic chromium, and has access to the body pool of chromium that responds to increases in blood insulin. The biologically active form of chromium (GTF) is an essential dietary agent that potentiates the action of insulin and thereby functions in regulating protein, fat and carbohydrate metabolism.

A particular form of GTF chromium, marketed under the name ChromeMate® by InterHealth Nutraceuticals, is a unique form of niacin-bound chromium (called chromium nicotinate or polynicotinate) that dramatically increases the effectiveness of chromium in the effects discussed above. Normally, chromium is poorly absorbed and utilized by the body. However, researchers have found that the most potent form of chromium in nature (i.e., the form that best activates insulin) is bound to the B vitamin niacin. In particular researchers have found that a patented oxygen-coordinated chromium-niacin complex is the most potent form of all, being over 18-times more potent than the next closest form of niacin-bound chromium tested. This oxygen-coordinated complex is characterized by chromium bound to an oxygen atom of the carboxylic acid group attached to niacin's pyridine ring structure.

As discussed above, chromium has been shown to reduce LDL cholesterol levels. In particular, administration of this oxygen-coordinated niacin-bound chromium complex (also designated O-NBC) in sufficient amounts has been shown to reduce LDL cholesterol in humans by an average of 14%. Researchers also have shown that O-NBC is significantly more bioavailable than chromium picolinate and chromium chloride. Supplementation with O-NBC therefore has been shown to ameliorate type II diabetes, reduce hypertension, decrease fat mass, and increase lean body mass, as well as help reduce body weight in persons consuming O-NBC. Additionally, high doses of O-NBC have been shown to be completely safe and non-toxic. In contrast, chromium picolinate has been shown to damage DNA and be mutagenic.

Previous studies also have shown the effectiveness of O-NBC in promoting weight loss. In a prior study, young obese women consuming 400 micrograms of chromium as O-NBC per day, in combination with exercise, experienced significant weight loss over an eight-week study period. In contrast, no change in weight was observed in subjects who exercised and consumed chromium in the form of chromium picolinate or a placebo. Also, subjects who consumed chromium picolinate and did not exercise experienced significant weight gain during the study period. In another study, overweight African-American women consuming 600 mcg of chromium daily as O-NBC for 8 weeks had a significant loss of body fat and sparing of muscle compared with a prior placebo period of the same duration. Increased fat loss also was observed among women who were randomized to consume O-NBC first, followed by placebo, suggesting a carry-over effect of the supplementation on fat loss. No adverse effects were observed from ingestion of O-NBC on the women in these studies.

Other known dietary supplements include plants in the genus *Gymnema*, such as *Gymnema sylvestre*, a traditional Ayurvedic herb known to balance elevated blood sugar levels. The active ingredients in *Gymnema sylvestre*, gymnemic acid and gurmarin, have molecular structures similar to that to glucose and possess a number of health benefits. Gurmarin has the ability to fill taste bud receptors and reduce the sweet taste of sugary foods, thus greatly reducing the craving for sweets. Gymnemic acid helps increase the production of insulin by stimulating the production of new insulin-producing cells, called beta-cells, in the pancreas. Gymnemic acid also facilitates insulin release from the beta-cells into the blood stream by increasing beta-cell membrane permeability. Gymnemic acid also inhibits the absorption of sugar molecules in the intestines during digestion, thus reducing increases in blood sugar levels. Finally, consumption of *Gymnema sylvestre* also has been shown to significantly lower cholesterol in animal models.

Each of the materials described above are known to exhibit weight control and/or other health promoting properties in persons or other mammals consuming them. However, individually, none provide all of the weight control and health promoting properties described above. It is apparent from the above that a need exists for improved methods and compositions for controlling body weight and improving the health condition of persons or other mammals prone to excess body weight, including improvement of body mass index (an indicator of healthy body weight), serum leptin levels, serum serotonin levels, and the cardiovascular risk factors total cholesterol, LDL cholesterol, HDL cholesterol and triglycerides. The present invention fulfills this need and provides further related advantages.

SUMMARY OF THE INVENTION

The present invention resides in a composition comprising hydroxycitric acid, chromium, and gymnemic acid. In preferred aspects of the invention, the hydroxycitric acid is bound to calcium and potassium. The hydroxycitric acid in the composition preferably is derived from a plant of the genus *Garcinia*, most preferably *Garcinia Cambogia*. The chromium in the composition preferably is niacin-bound chromium, and more preferably oxygen-coordinated niacin-bound chromium. The gymnemic acid in the composition preferably is derived from a plant of the genus *Gymnema*, most preferably *Gymnema sylvestre*. The composition may be in the form of a pill, tablet, capsule, lozenge, gum, liquid, powder, food, beverage or other orally administered form.

The present invention also resides in related methods for increasing serotonin level, decreasing leptin level, or increasing fat oxidation in a person or other mammal, incorporating identifying a person or other mammal that can benefit from increased serotonin level, decreased leptin level and/or increased fat oxidation, and administering to the person or other mammal a composition comprising hydroxycitric acid in an amount sufficient to provide the required effect. Preferred aspects of the method incorporate administration of hydroxycitric acid in forms as described above. The method preferably incorporates administering approximately 100 milligrams to approximately 5,000 milligrams of hydroxycitric acid daily, and more preferably approximately 2,700 milligrams to approximately 2,800 milligrams. In the method, the composition preferably is administered daily in three substantially equally divided doses, approximately 30 to 60 minutes before meals, preferably orally. In preferred aspects of the method, the composition also incorporates chromium and gymnemic acid in forms as described above. Preferably, the method incorporates administering approximately 10 micrograms to approximately 1,000 micrograms of chromium and approximately 10 milligrams to approximately 1,000 milligrams of gymnemic acid daily, and more preferably approximately 400 micrograms of chromium and approximately 100 milligrams of gymnemic acid daily.

The present invention also resides in related methods for providing the following effects in a person or other mammal: reducing excess, or maintaining healthy, body weight or body mass index; decreasing appetite and reducing food intake; and/or decreasing total cholesterol, LDL cholesterol and/or triglyceride levels, and/or increasing HDL cholesterol levels. The methods incorporate identifying a person or other mammal suffering, or at risk for suffering, from excess body weight, excess body mass index, elevated total cholesterol level, elevated LDL cholesterol level, elevated triglyceride level and/or reduced HDL cholesterol level; and administering to the person or other mammal a composition incorporating hydroxycitric acid, chromium and gymnemic acid in an amount sufficient to provide the required effect. The hydroxycitric acid, chromium and gymnemic acid preferably are in the forms described above. Preferably, the composition administered incorporates approximately 100 milligrams to approximately 5,000 milligrams of hydroxycitric acid, approximately 10 micrograms to approximately 1,000 micrograms of chromium, and approximately 10 milligrams to approximately 1,000 milligrams of gymnemic acid daily, and more preferably approximately 2,700 milligrams to approximately 2,800 milligrams of hydroxycitric acid, approximately 400 micrograms of chromium, and approximately 100 milligrams of gymnemic acid daily. Preferably, the method incorporates administering the composition daily in three substantially equally divided doses, approximately 30 to 60 minutes before meals, preferably orally.

DETAILED DESCRIPTION OF THE PREFERRED EMBODIMENTS

The present invention resides compositions incorporating (−)-hydroxycitric acid (HCA), chromium and gymnemic acid. The present invention also resides in methods for controlling body weight and improving the above-discussed health factors of persons or other mammals, including increasing serum serotonin levels, reducing serum leptin levels, increasing fat oxidation, reducing food intake, lowering body mass index (BMI), and improving cardiovascular risk factors by decreasing elevated total and LDL cholesterol, increasing HDL cholesterol and reducing elevated triglyceride levels. The methods include identifying a person or other mammal who is, or is at risk for being, overweight, or who would benefit from the above-described physiological changes, and administering to the person or other mammal a composition comprising sufficient amounts to effect the changes. The present invention also resides in a composition which, when administered to a person or other mammal, provides for the above-described psychological changes, the composition comprising a salt of HCA and other selected components.

The HCA used in the compositions preferably is in a form incorporating both calcium and potassium, to provide for superior solubility, bioavailability, and commercial utility. In preferred methods of the present invention, the composition administered also incorporates: chromium, preferably from oxygen-coordinated niacin-bound chromium, and *Gymnema sylvestre* extract, providing gymnemic acid and gurmarin. Preferably, the method involves administering a composition incorporating approximately 100 to 5,000 milligrams, and more preferably 2,700 to 2,800 milligrams, of HCA daily to a person or other mammal who would benefit from the physiological changes discussed above. The preferred composition to be administered also can incorporate approximately 10 to 1,000 micrograms, and most preferably 400 micrograms, of elemental chromium daily, preferably from oxygen-coordinated niacin-bound chromium, and approximately 10 to 1,000 milligrams, and most preferably 400 milligrams, *Gymnema sylvestre* extract providing approximately 5 to 500 milligrams, and most preferably 100 milligrams, of gymnemic acid daily.

The methods of the present invention provide for the safe, effective and convenient reduction of excess body weight and resulting reduction in body mass index (BMI), or maintenance of healthy body weight and healthy BMI, in persons or other mammals. Besides these effects, administration of the compositions also provides for reducing serum leptin levels, increasing serum serotonin levels, reducing food intake, increasing fat oxidation, decreasing elevated total and LDL cholesterol, increasing HDL cholesterol, and reducing elevated triglyceride levels in persons or other mammals that would benefit from such effects.

It has been surprisingly found that compositions incorporating the components discussed above increase serum serotonin levels, reduce serum leptin levels and increase fat oxidation. It has also been surprisingly found that optimal concentrations of HCA exist for maximizing serum serotonin levels, a possible mechanism for decreasing appetite and reducing food intake. Another surprising finding is that compositions incorporating the components described above provide for superior improvement in reducing excess body weight and improving the related health factors described herein than was expected based on the previously know properties of the components. Specifically, the combination of HCA, chromium and gymnemic acid was shown to reduce body weight, lower body mass index, increase serum serotonin levels, reduce food intake, reduce serum leptin levels, increase fat oxidation, decrease harmful total and LDL cholesterol, increase beneficial HDL cholesterol and lower triglycerides significantly greater than HCA alone.

Preferred administration of the composition is orally, in three equally-divided doses roughly 30 to 60 minutes before meals administered daily. The composition also can include inert ingredients or diluents, such as sugar, maltodextrin, cellulose, or other inert ingredients commonly used in food and beverage products. The composition may be in various forms commonly used for dietary supplements, including pill, tablet, capsule, lozenge, gum, food, liquid, or powder. The composition also can be incorporated into food or beverage products, including bars, shakes, gums, beverages, or other processed or prepared food or beverage products, or any other orally administerable form.

Use of the methods and compositions of the present invention is illustrated in the Example below.

EXAMPLE

The effects of administering compositions within the scope of the methods of the present invention were tested. A double-blind, placebo-controlled human clinical trial was conducted using a composition incorporating: the HCA-SX extract described above (Super CitriMax™, supplied by InterHealth Nutraceuticals of Benicia, Calif.); and HCA-SX extract in combination with chromium (ChromeMate®, supplied by InterHealth), and *Gymnema sylvestre* extract (also supplied by InterHealth).

82 moderately obese human subjects completed the study. All subjects were placed on a daily diet of 2,000 kcal. All food was prepared and delivered to the subjects, and all food intake was strictly supervised by trained dieticians. All subjects also underwent a 30 minute walking exercise program, five times a week, which was supervised by a trained exercise specialist. The subjects were randomly divided into three groups. The subjects in the first group were given a placebo. The subjects in the second group was given a daily dose of 4,667 mg of *Garcinia cambogia* extract (providing 2,800 mg HCA per day). The subjects in the third group were given a daily dose of 4,667 mg of a combination of *Garcinia cambogia* (2,800 mg HCA), 4 mg of niacin-bound chromium (providing 400 mcg of elemental chromium), and 400 mg of *Gymnema sylvestre* extract (providing 100 mg gymnemic acid). The subjects received their respective compositions in three equally-divided doses 30 to 60 minutes before breakfast, lunch and dinner for eight weeks. These dosage levels of HCA were determined by extrapolation of successful earlier animal trials, as well as review of optimal micromolar concentrations of HCA in ex vivo brain tissue resulting in maximum serotonin release. Changes in body weight, lipid profile (triglycerides, LDL, HDL and total cholesterol), obesity gene level (determined by serum leptin level), serum serotonin levels, body mass index, fat metabolites (urinary malondialdehyde, formaldehyde, acetaldehyde and acetone levels) and appetite control were assessed in the persons. These changes were averaged to produce figures for analysis.

Results

Results of the testing are shown in Table 1 below.

TABLE 1

Results of Administration of Compositions

| Tested Factor | Placebo | HCA-SX | HCA-SX + chromium + gymnemic acid |
|---|---|---|---|
| Body Weight | | | |
| Pounds | 3.5 | 10.0 | 12.8 |
| % change | 1.9 | 5.0 | 6.5 |
| LDL Cholesterol | | | |
| mg/dl | 3.0 | −14.5 | −22.6 |
| % change | 2.8 | −13.0 | −19.0 |
| HDL Cholesterol | | | |
| mg/dl | −0.7 | 2.7 | 6.2 |
| % change | −2.7 | 9.0 | 21.4 |
| Total Cholesterol | | | |
| mg/dl | 1.1 | −12.4 | −16.6 |
| % change | 1.0 | −7.4 | −9.7 |
| Triglycerides | | | |
| mg/dl | 0.3 | −12.9 | −22.6 |
| % change | 0.3 | −10.0 | −19.0 |
| Serum Leptin Level | | | |
| ng/ml | 0.4 | −12.2 | −15.4 |
| % change | 1.0 | −40.0 | −42.6 |
| Serum Serotonin Level | | | |
| mg/dl | 20.1 | 119.1 | 149.3 |
| % change | 10.9 | 48.5 | 70.4 |
| Body Mass Index | | | |
| kg/m$^2$ | −0.7 | −2.4 | −3.2 |
| % change | −2.0 | −7.0 | −9.2 |
| Excreted Fat Metabolites % change | | | |
| Acetone | 3.5 | 36.2 | 42.8 |
| Formaldehyde | 8.8 | 68.1 | 52.7 |
| Malonaldehyde | 12.6 | 60.6 | 65.3 |
| Acetaldehyde | 18.1 | 64.4 | 73.0 |

TABLE 1-continued

Results of Administration of Compositions

| Tested Factor | Placebo | HCA-SX | HCA-SX + chromium + gymnemic acid |
|---|---|---|---|
| Food Intake Reduction | | | |
| grams per day (average) | 0 | 257 | 386.2 |
| % change | 0 | 11.4 | 17.2 |

Discussion

The data from the study show that administration of the specified levels of HCA extract results in: significant weight loss; decreases in body mass index (an index of obesity health risk); reductions in triglycerides, LDL and total cholesterol (cardiovascular risk factors); increases in beneficial HDL cholesterol; increases in excretion of fat metabolites (indicating increased fat oxidation or "burning"); decreases in serum leptin levels (a biomarker of the obesity gene); increases in serum serotonin levels (a mechanism of appetite control and eating behavior); and, reductions in food intake. Further, the composition incorporating all three components (HCA-SX, chromium and gymnemic acid) resulted in even greater improvement in all of the tested factors than use of the composition incorporating HCA-SX alone.

A number of interesting findings are observed from the results presented above. The constituents of the compositions demonstrated multifaceted activities, which collectively resulted in a number of health benefits. Also, none of the constituents activated the central nervous system, demonstrating the relative safety of the compositions over, for example, ephedra-containing weight management formulas. HCA-SX exhibited its predominant effect on the biochemical regulation of leptin, which is an integral key component of obesity regulatory genes. Serotonin level also was modulated by HCA-SX alone, but it was more effectively modulated by the combination of HCA-SX, chromium, and gymnemic acid. The effect of serotonin level modulation was reflected in the reduced appetite in the study subjects.

An examination of the lipid profile data clearly shows that HCA-SX alone lowers LDL and triglyceride levels and increases HDL levels, however, the combination of HCA, chromium and gymnemic acid exhibited even greater changes in these key components. Also, a high correlation exists between increased fat oxidation and enhanced excretion of urinary lipid metabolites with a dramatic reduction in the triglyceride level. Glycerol is a product of the metabolism of triglycerides by adipose tissue and other brown tissues that possess a high glycerol kinase level. Glycerol kinase can activate the breakdown of triglycerides to glycerol, leading to enhanced formation of formaldehyde via microsomal metabolism. This indicates that the compositions of the present invention can provide for enhanced biochemical induction of glycerol kinase, which can serve to enhance two important biochemical functions: biochemical reduction of triglyceride levels, and fat oxidation.

Although the invention has been disclosed in detail with reference only to the preferred embodiments, those skilled in the art will appreciate that additional methods and compositions can be made without departing from the scope of the invention.

We claim:

1. A method for increasing fat oxidation in a person or other mammal comprising: identifying a person or other mammal that can benefit from increased fat oxidation; and administering to the person or other mammal a composition comprising hydroxycitric acid in an amount sufficient to increase fat oxidation in the person or other mammal wherein the increase in fat oxidation is manifested by increases in the production of one or more urinary metabolites selected from the group consisting of malondialdehyde, formaldehyde, acetaldehyde and acetone.

2. A method as defined in claim 1, wherein the composition comprises hydroxycitric acid derived from a plant of the genus *Garcinia*.

3. A method as defined in claim 2, wherein the plant is *Garcinia cambogia*.

4. A method as defined in claim 1, wherein the step of administering comprises administering approximately 100 milligrams to approximately 5,000 milligrams of hydroxycitric acid daily.

5. A method as defined in claim 4, wherein the step of administering comprises administering approximately 2,700 milligrams to approximately 2,800 milligrams of hydroxycitric acid daily.

6. A method as defined in claim 1, wherein the step of administering comprises administering the composition daily in three substantially equally divided doses, approximately 30 to 60 minutes before meals.

7. A method as defined is claim 1, wherein the step of administering comprises administering the composition orally.

8. A method as defined in claim 1, wherein the composition further comprises chromium and gymnemic acid.

9. A method as defined in claim 8, wherein the composition comprises niacin-bound chromium.

10. A method as defined in claim 9, wherein the composition comprises oxygen-coordinated niacin-bound chromium.

11. A method as defined in claim 10, wherein the composition comprises gymnemic acid is derived from a plant of the genus *Gymnema*.

12. A method as defined in claim 11, wherein the plant is *Gymnema sylvestre*.

13. A method as defined in claim 8, wherein the step of administering comprises administering approximately 10 micrograms to approximately 1,000 micrograms of chromium and approximately 10 milligrams to approximately 1,000 milligrams of gymnemic acid daily.

14. A method as defined in claim 13, wherein the step of administering comprises administering approximately 400 micrograms of chromium and approximately 100 milligrams of gymnemic acid daily.

15. A method as defined in claim 1, wherein the composition comprises hydroxycitric acid bound to calcium and potassium.

* * * * *